United States Patent [19]

Brooks

[11] Patent Number: 4,767,409
[45] Date of Patent: Aug. 30, 1988

[54] CATHETER PROTECTIVE SHIELD

[75] Inventor: Frederick C. Brooks, Athens, Tex.

[73] Assignee: Edward Weck Incorporated, Princeton, N.J.

[21] Appl. No.: 497,324

[22] Filed: May 23, 1983

[51] Int. Cl.⁴ .............................................. A61M 5/00
[52] U.S. Cl. .................................. 604/171; 604/163; 604/283
[58] Field of Search ........................ 604/171, 163, 283

[56]  References Cited
U.S. PATENT DOCUMENTS

| | | | |
|---|---|---|---|
| 2,937,643 | 5/1960 | Elliot | 604/163 |
| 3,154,080 | 10/1964 | Rowan et al. | 604/171 |
| 4,235,232 | 11/1980 | Spaven et al. | 604/171 X |
| 4,326,520 | 5/1982 | Alley | 604/171 |

Primary Examiner—Stephen C. Pellegrino
Attorney, Agent, or Firm—Lawrence S. Levinson; Robert E. Lee, Jr.

[57]  ABSTRACT

The catheter protective shield is used to protect a flow directed catheter of the type used in the measurement of central venous pressure and pulmonary wedge pressure. The cathetershield assembly includes front and rear hubs sized to permit movement of the catheter therethrough and an external support tube for interconnecting the front and rear hubs. A flexible protective sleeve interconnects the two hubs. The protective sleeve is substantially longer than the external support tube and is collapsible to permit interconnection of the hubs by the external support tube and may be extended to shield a substantial length of catheter.

7 Claims, 2 Drawing Sheets

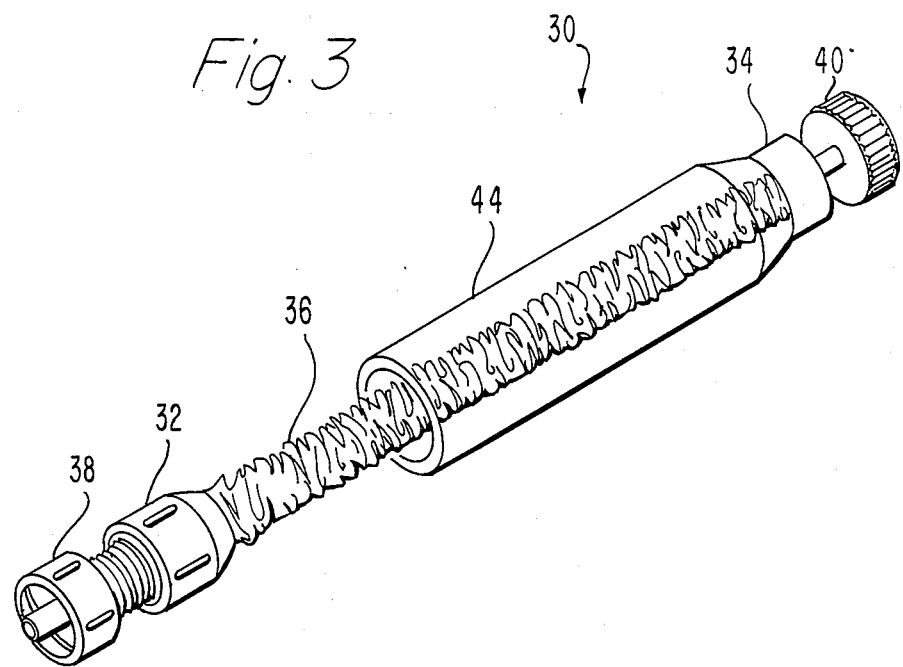
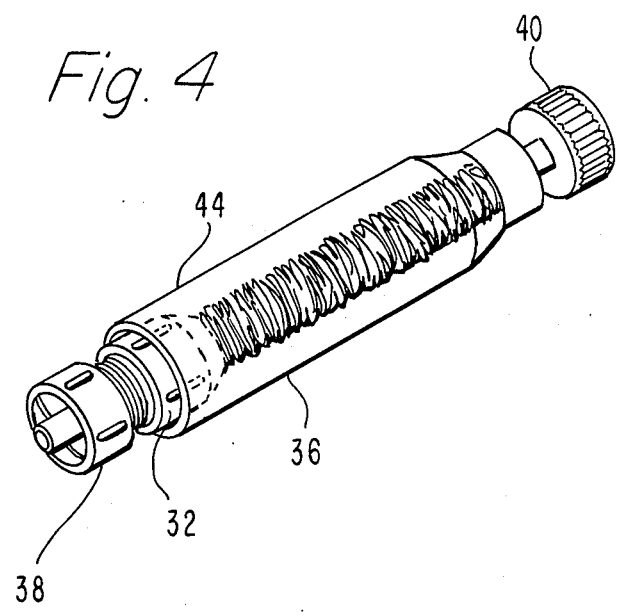

CATHETER PROTECTIVE SHIELD

BACKGROUND OF THE INVENTION

The present invention relates to a device used to protect a catheter from contamination during and after the time the catheter is inserted into a venous lumen or other body cavity.

The invention is particularly useful for the protection of flow directed catheters used in the measurement of central venous pressure and pulmonary wedge pressure during and after cardio-pulmonary bypass surgical procedures. In these procedures, the patient is monitored using a pulmonary artery balloon tipped catheter having at least two lumens. The catheter is placed percutaneously before induction of anesthesia. In certain instances, it has been observed that the balloon of the catheter will fail to wedge after cardio-pulmonary bypass and the catheter has to be repositioned. Manipulation of the catheter to reposition it is recognized to the hazardous, because, over a period of time, exposed segments of the catheter may become contaminated, and introduction of the exposed portion may cause infection.

As is well known, a catheter is inserted through a vein, such as the right internal jugular vein or the subclavian vein, of the patient by inserting a hollow needle through which a stainless steel guide wire is then introduced into the lumen of the vein. A dilator and introducer system is then placed over the guide wire and into the vessel (i.e., Seldinger Technique). The dilator and guide wire are then removed, and the flow directed catheter is inserted and positioned through the introducer device. The normal practice also involves the use of a plastic protective sleeve which is tied or otherwise secured at one end to the introducer prior to introducing the catheter.

After the catheter has been completely advanced to the wedge position, the opposite end of the protective sleeve is fully extended over the catheter to a position remote from the introducer. This end is then fastened in place by a sterile fastening, so a length of catheter between the introducer and the opposite end of the protective sleeve is protected from contamination. The protected portion, which may be as long as 40 inches (100 cm.), can be advanced easily into the vein if the catheter again has to be moved to the wedge position due to dislodgement or migration.

Heretofore, there have been efforts made to incorporate a protective sleeve extending between a front hub and a rear hub, with a disconnectible guide tube means within the flexible protective sleeve. The guide tube facilitates feeding a catheter through the assembly comprising the plastic protective sleeve which extends between the pair of hubs, particularly when used with an adapter with a side port and a catheter introducer. Such efforts are shown in U.S. Pat. No. 4,327,723 entitled CATHETER SHIELD and in U.S. Pat. No. 4,327,735 entitled CATHETER ASSEMBLY, which patents are incorporated herein by reference to show both the state of the art and the manner in which a protective catheter shield assembly is used.

The devices described in the aforementioned patents failed to provide means for firmly connecting the catheter shield assembly to a catheter, in order to prevent movement of the catheter shield assembly along the catheter. In particular, one of the devices used rubber hubs with a hole bored through them, and the other device used a rubber band to hold the protective sleeve in place on the catheter. In both of these devices, the protective sleeve was found to slip on the catheter. In addition, the devices heretofore known used an internal feed tube through which a catheter was advanced. Disadvantages of the internal feed tube are that its internal diameter limits the external diameter of a catheter which can be passed therethrough, and that it fails to protect the flexible protective sleeve, which is left exposed. Accordingly, an improved apparatus for catheter placement and protection would be desirable.

SUMMARY OF THE INVENTION

The present invention is a device which provides for the protection from contamination of a length of an indwelling catheter, thereby providing a reserve catheter portion which can be advanced into the body should the catheter require repositioning. The invention provides a simplified means of preventing contamination of a section of catheter within a protective sleeve, so that the catheter can be easily and safely advanced into a patient's body in the event that the catheter is dislodged or migrates without fear of contaminating the patient.

The invention is comprised of a front hub, a rear hub, and an interconnecting, elongated, collapsible, flexible protective sleeve of transparent plastic material which is secured to and sealed to the periphery of the front and rear hubs. The two hubs are connected by an external support tube means preferably comprising a clear feed tube secured to one of the hubs and frictionally connected to the other hub. When interconnected, the length of the assembly is substantially shorter than the length of the flexible, transparent plastic protective sleeve. The rear hub is provided with an opening for advancement of a catheter through the protective sleeve and through the front hub for subsequent feeding into an introducer for insertion into the patient's body. Sealing means are provided at the front and rear hubs to prevent the migration of contaminants, such as microbiological contaminants, into the shield portion of the protective sleeve. Preferably, just prior to insertion into the patient's body, while all parts are still in a sterile condition, the protective sleeve is extended so as to provide a reserve length of catheter which is always then protected from touch contamination.

BRIEF DESCRIPTION OF THE DRAWING

In the Drawing:

FIG. 3 is a perspective view of a second embodiment of the catheter protective shield of the present invention in with the flexible protective sleeve extended; and FIG. 4 is a perspective view of the embodiment of FIG. 3 in the closed position.

DESCRIPTION OF THE PREFERRED EMBODIMENTS

Figure 1:
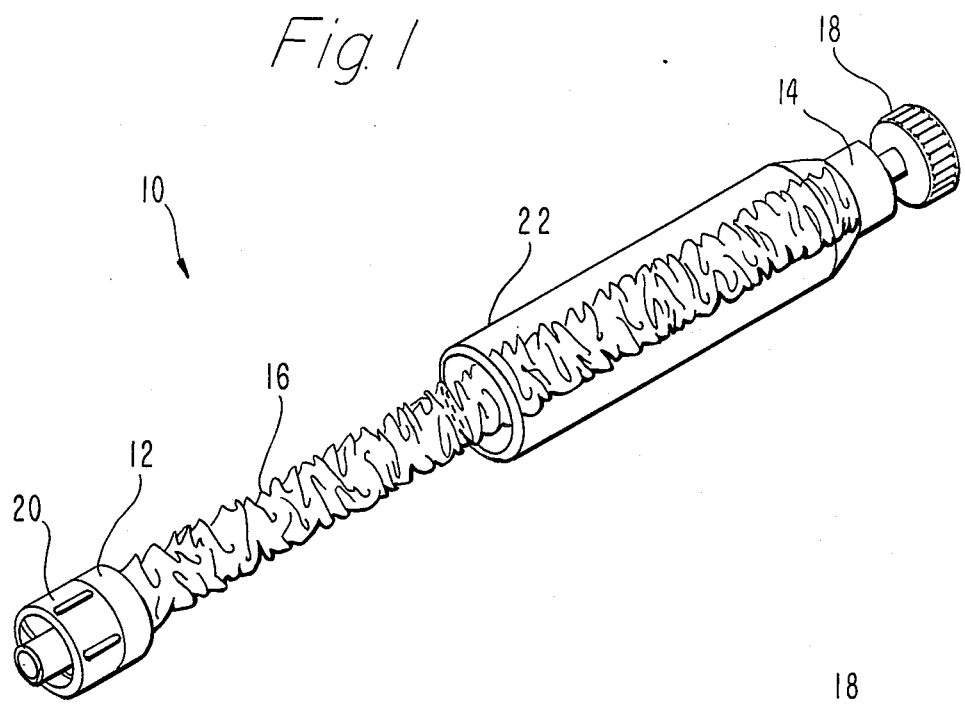
FIG. 1 is a perspective view of a first embodiment of the catheter protective shield of the present invention in with the flexible protective sleeve extended.
Figure 2:
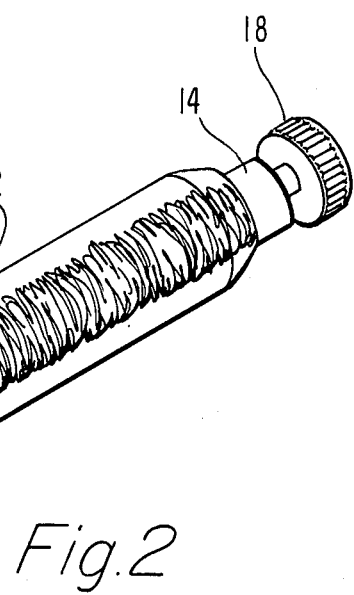
FIG. 2 is a perspective view of the embodiment of FIG. 1 in the closed position.

Referring now to FIGS. 1 and 2, there is shown a first embodiment of the catheter shield assembly 10 of the present invention. The catheter protective shield 10 is comprised of a front hub 12 and a rear hub 14. The hubs 12, 14 are connected together by a flexible protective sleeve 16, which is typically constructed of a clear, flexible, sterilizable plastic. Connected, also, to the hubs 12, 14 are means for connecting the catheter protective shield 10 to a catheter and to catheter introducer apparatus (not shown). In the present embodiment of the invention, the means for connecting the catheter protective shield 10 to the rear hub 14 is a Tuohy Borst mechanism 18, and the means for connecting the front hub 12 to the introducer apparatus is a Luer lock connector 20, although other connective means can be used, as will be explained hereinafter. The present invention further comprises an external support tube 22, comprised, in the present embodiment of a rigid, clear plastic tube which is attached to the rear hub 14. The internal shape and dimensions of the support tube 22 and the external shape and dimensions of the front hub 12 are such that the support tube 22 can be press fit over the front hub 12, thereby connecting the two hubs 12, 14, with the flexible protective sleeve 16 contained within the external support tube 22, as shown in FIG. 2.

In use, a physician can connect the Luer lock fitting 20 on the catheter protective shield 10 to a catheter introducer, having a female Luer lock fitting thereon, which has been inserted into the selected vein and taped in place. A catheter which is normally preassembled with the catheter protective shield 10, is advanced through the rear hub 14, through the flexible protective sleeve 16 and out through the front hub 12. The catheter is advanced until the desired length indicator mark is visible on its periphery, in a manner well known in the art and described more fully in the aforementioned patents. The catheter can then be tested for balloon integrity in the normal manner before the Luer lock fittings of the introducer and the catheter protective shield 10 are then connected.

As soon as the tip of the catheter is introduced, the balloon is typically inflated and the catheter is gently advanced to the wedge position. At this point there is typically about 5 inches of exposed catheter between the side port assembly of the introducer assembly and the front hub 12 of the catheter protective shield 10. The rear hub 14 is then pulled backward so that the external support tube 22 disconnects from the front hub 14, leaving the flexible protective sleeve 16 covering a length of catheter which is to be protected from contamination. Contamination is thus prevented from the introducer back to the opening in the Tuohy Borst mechanism 18. Should it become necessary to reposition the catheter, the reserve length of catheter within the flexible, protective sleeve 16 is available to be advanced into the patient's body reducing the risk of contamination. The transparency of the protective sleeve 16 permits ready viewing of the length markings on the catheter so that the length of catheter within the patient can be readily determined.

Referring now to FIGS. 3 and 4, a second embodiment 30 of the present invention is shown. In this embodiment the catheter protective shield 30 is comprised of a front hub 32 and a rear hub 34. The hubs 32, 34 are connected together by a flexible protective sleeve 36, which is typically constructed of a clear, flexible, sterilizable plastic. Connected, also, to the hubs 32, 34 are means for connecting the catheter protective shield 30 to a catheter and to catheter introducer apparatus (not shown). In this embodiment of the invention, the means connected to the front and rear hubs 34, 36 are Tuohy Borst mechanisms 38, 40. The present embodiment of the invention further comprises an external support tube 42, comprised of a rigid, clear plastic tube which is attached to the rear hub 34. The internal shape and dimensions of the support tube 42 and the external shape and dimensions of the front hub 32 are such that the support tube 42 can be press fit over the front hub 32, thereby connecting the two hubs 32, 34 with the flexible protective sleeve 36 contained within the external support tube 42 as shown in FIG. 4.

In using this embodiment of the invention, a physician can connect the Tuohy Borst mechanism 38 on the front hub 32 of the catheter protective shield 30 directly to a catheter. Otherwise, the present embodiment 30 is used substantially in the same manner as the first embodiment of the invention 10, described above.

I claim:

1. A catheter protective shield for an indwelling catheter comprising:
   (a) front and rear hubs having central passages, said passages each being sized an indwelling permit movement of said catheter through said hubs;
   (b) a flexible protective sleeve interconnecting the two hubs, said protective sleeve providing a continuous, protective covering for a catheter which extends between said hubs;
   (c) an external support tube adapted to interconnect said hubs, said external support tube having a length which is substantially shorter than the length of said flexible protective sleeve, whereby said flexible protective sleeve is enclosed by said external support tube when said external support tube interconnects said hubs.

2. The catheter protective shield of claim 1 further comprising means connected to said front hub for connecting said catheter protective shield to a catheter introducer.

3. The catheter protective shield of claim 2 wherein said means connected to said front hub for connecting said catheter protective shield to a catheter introducer comprises a Tuohy Borst mechanism.

4. The catheter protective shield of claim 2 wherein said means connected to said front hub for connecting said catheter protective shield to a catheter introducer comprises a Luer lock mechanism.

5. The catheter protective shield of claim 1 further comprising means connected to said rear hub for connecting said catheter protective shield to a catheter.

6. The catheter protective shield of claim 2 wherein said means connected to said rear hub for connecting said catheter protective shield to a catheter introducer comprises a Tuohy Borst mechanism.

7. The catheter protective shield of claim 2 wherein said means connected to said rear hub for connecting said catheter protective shield to a catheter introducer comprises a Luer lock mechanism.

* * * * *

UNITED STATES PATENT AND TRADEMARK OFFICE
CERTIFICATE OF CORRECTION

PATENT NO. : 4,767,409

DATED : August 30, 1988

INVENTOR(S) : Frederick C. Brooks

It is certified that error appears in the above-identified patent and that said Letters Patent are hereby corrected as shown below:

Column 1, line 20, after "recognized to" the word "the" should be replaced by the word --be--.

Column 4, line 25, the words "an indwelling" should be replaced with --to--.

Column 4, line 26, the word "said" before "catheter" should be replaced with --an indwelling--.

Signed and Sealed this

Third Day of January, 1989

*Attest:*

DONALD J. QUIGG

*Attesting Officer*    *Commissioner of Patents and Trademarks*